(12) United States Patent
Church et al.

(10) Patent No.: US 8,530,156 B2
(45) Date of Patent: Sep. 10, 2013

(54) CHEMICALLY CLEAVABLE PHOSPHORAMIDITE LINKERS FOR SEQUENCING BY LIGATION

(75) Inventors: George M. Church, Brookline, MA (US); A. Michael Sismour, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 755 days.

(21) Appl. No.: 12/533,439

(22) Filed: Jul. 31, 2009

(65) Prior Publication Data

US 2010/0081140 A1 Apr. 1, 2010

Related U.S. Application Data

(60) Provisional application No. 61/087,236, filed on Aug. 8, 2008.

(51) Int. Cl.
*C12Q 1/68* (2006.01)
*C12P 19/34* (2006.01)
*C07H 21/04* (2006.01)
*C07H 19/04* (2006.01)

(52) U.S. Cl.
USPC ......... 435/6.1; 435/91.1; 435/91.2; 536/24.3; 536/26.6

(58) Field of Classification Search
USPC ............... 435/6.1, 91.1, 91.2; 536/24.3, 26.6
See application file for complete search history.

(56) References Cited

U.S. PATENT DOCUMENTS

| | | | |
|---|---|---|---|
| 5,750,341 A | 5/1998 | Macevicz | |
| 6,306,597 B1 | 10/2001 | Macevicz | |
| 2008/0003571 A1* | 1/2008 | McKernan et al. | 435/6 |

FOREIGN PATENT DOCUMENTS

WO  WO9627025  *  9/1996

OTHER PUBLICATIONS

Shendure et al, Science, 2005, 309:1728.
Shendure et al, Nat. Rev., 2004, 5:335.
Mitra et al, Anal. Biochem, 2003, 320:55.
Ronaghi et al, Science, 1998, 281:363.
Brenner et al, Nat. Biotech, 2000, 18:630.

* cited by examiner

*Primary Examiner* — Jezia Riley
(74) *Attorney, Agent, or Firm* — Banner & Witcoff, Ltd.

(57) ABSTRACT

Linkers and methods for determining a nucleotide sequence of a reference oligonucleotide are provided.

64 Claims, 4 Drawing Sheets
(2 of 4 Drawing Sheet(s) Filed in Color)

1A

1B

1C

1A

1B

1C

CHEMICALLY CLEAVABLE PHOSPHORAMIDITE LINKERS FOR SEQUENCING BY LIGATION

This application claims priority to U.S. Provisional Patent Application No. 61/087,236, filed on Aug. 8, 2008 and is hereby incorporated herein by reference in its entirety for all purposes.

STATEMENT OF GOVERNMENT INTERESTS

This invention was made with Government support under GM808988 and HG003170 awarded by the National Institutes of Health. The Government has certain rights in the invention.

FIELD

The present invention relates to novel linkers and novel methods for sequencing by ligation.

BACKGROUND

Methods for 'next generation' (e.g., polony) sequencing typically employed in the art use degenerate oligonucleotides (e.g., octamers and nonamers) and protein ligases to discriminate among oligonucleotides with perfect match at one or more positions relative to mismatched oligonucleotides (see Shendure et al. (2005) *Science* 309:1728; SOLiD™ (Applied Biosystems, Foster City, Calif.); and Complete Genomics (Mountain View, Calif.)). These technologies can accurately read six nucleotides in from the ligation junction. The current method to increase read-length beyond six bases uses degenerate oligonucleotides containing a cleavable bridged phosphorothioate internucleotide linkage between positions 6 and 7 from the ligation junction (e.g., SOLiD™ (Applied Biosystems)). After ligation to the anchor oligonucleotide bound to the immobilized template, the solid phase is extensively washed to remove free fluor-oligonucleotides and visualized with a digital camera. The oligonucleotides are typically labeled with fluorophores so that a given emission wavelength corresponds with a given base (or bases) (e.g., A, C, G or T) at specific locations in the oligonucleotide bound to the template (e.g., unknown) DNA. Following imaging, the bridged phosphorothioate internucleotide linkage is cleaved, releasing the fluorophores and truncating the oligonucleotide. A subsequent round of degenerate oligonucleotides are ligated, washed and imaged to determine the sequence on positions 7-12 on the template (e.g., using SOLiD™ (Applied Biosystems)).

The main obstacle for increasing read-length in this manner is the synthesis on the oligonucleotides containing the bridged-phosphorothioate internucleotide linkage. These oligonucleotides require commercially unavailable nucleoside phosphoramidites that are expensive to synthesize. In addition, the current technology only allows sequencing in one direction.

SUMMARY

The present invention is based in part on the discovery of a novel class of phosphoramidite (e.g., phosphoramidite 1) linkers which, when incorporated into a nucleic acid sequence (e.g., an oligonucleotide sequence) via standard solid phase oligonucleotide synthesis, allows chemical removal of a linker and any moiety optionally attached to the linker from the nucleic acid sequence. The novel cleavable linkers described herein (e.g., phosphoramidite 1 linkers) are economically synthesized. The present invention is also based in part on the discovery of novel methods that use existing phosphoramidites (e.g., phosphoramidite 2) that, when incorporated into an oligonucleotide sequence via a modified solid phase oligonucleotide synthesis scheme, allow chemical removal of the linker and any moiety attached to the linker from the oligonucleotide leaving a phosphate group at the 3' and/or 5' end of the oligonucleotide.

The methods and compositions described herein are particularly useful for increasing the read length during nucleic acid (e.g., DNA) sequencing by employing degenerate oligonucleotides (e.g., hexamers) capped with a cleavable linker between the oligonucleotide and a detectable signal (e.g., a fluorophore). The cleavable linker prevents chain ligation and allows release of the detectable signal. This novel method also allows for sequencing in both directions, leading to a two-fold increase in read length over current technology.

Accordingly, in certain exemplary embodiments, a method of determining a nucleotide sequence of a reference oligonucleotide is provided. In certain embodiments, the method includes the steps of providing a reference oligonucleotide, providing a probe oligonucleotide having a detectable label bound to its 5' phosphate group via a cleavable linker, allowing the probe oligonucleotide to hybridize to the reference oligonucleotide, detecting the detectable label, and chemically cleaving the cleavable linker to remove the detectable label and to allow the probe oligonucleotide to have a 5' phosphate group. In other embodiments, the method includes the steps of providing a reference oligonucleotide, providing a probe oligonucleotide having a detectable label bound to its 3' end via a cleavable linker, allowing the probe oligonucleotide to hybridize to the reference oligonucleotide, detecting the detectable label, and chemically cleaving the cleavable linker to remove the detectable label to allow the probe oligonucleotide to have a 3' phosphate group.

In certain aspects, the method includes one or more additional sets of steps including providing an additional probe oligonucleotide having a detectable label bound to its 3' end via a cleavable linker, allowing the additional probe oligonucleotide to hybridize to the reference oligonucleotide and bind the 3' end of the previously hybridized probe, detecting the detectable label, and chemically cleaving the cleavable linker to remove the detectable label to allow the additional probe oligonucleotide to have a 3' phosphate group. In certain aspects, the method includes one or more additional sets of steps including providing an additional probe oligonucleotide having a detectable label bound to its 5' end via a cleavable linker, allowing the additional probe oligonucleotide to hybridize to the reference oligonucleotide and bind the 5' phosphate group of the previously hybridized probe, detecting the detectable label, and chemically cleaving the cleavable linker to remove the detectable label to allow the additional probe oligonucleotide to have a 5' phosphate group.

In certain aspects, the aliphatic backbone is between 2 and 24 carbons in length and/or includes at least one amide group, ether group, ketone group or ester group. In certain aspects, the cleavable linker is a phosphoramidite linker such as a phosphoramidite 1 linker, e.g., Compound II, Compound III or Compound IV or a commercially available phosphoramidite linker (e.g., phosphoramidite 2 linkers). In other aspects, the chemically cleaving step includes contacting the cleavable linker with one or more of $AgNO_3$ and $I_2$. In yet other aspects, the probe oligonucleotide contains the same number of nucleotides after chemically cleaving the cleavable linker as it contained prior to cleavage. In certain aspects, the detectable label is a fluorophore. In still other aspects, the probe oligonucleotide is a hexamer.

In certain exemplary embodiments, a method of rendering reactive a blocked 5' phosphate group of an oligonucleotide is provided. The method includes the steps of: providing an oligonucleotide having a blocked 5' phosphate group, wherein the oligonucleotide includes a cleavable linker bound to the 5' phosphate group, and chemically cleaving the cleavable linker from the oligonucleotide to expose the 5' phosphate group and render it reactive. In certain aspects, the chemically cleaving step includes contacting the cleavable linker with one or more of AgNO$_3$ and I$_2$. In other aspects, the cleavable linker is a phosphoramidite linker such as, e.g., Compound II, Compound III or Compound IV.

In certain exemplary embodiments, Compound I, having the formula C$_{30}$H$_{41}$(CH$_2$)$_x$N$_2$O$_4$PS where x=2-24 and the compound contains a P—S bond is provided. The P—S bond is not present in the phosphoramidite 2 linkers.

In certain exemplary embodiments, Compound II, having the formula

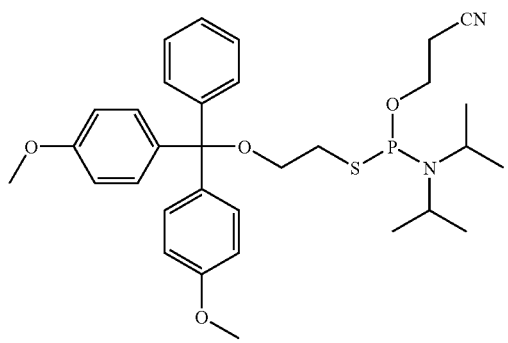 [SMILES: COc1ccc(C(OCCSP(OCCC#N)N(C(C)C)C(C)C)(c2ccccc2)c2ccc(OC)cc2)cc1]

is provided.

In certain exemplary embodiments, Compound III, having the formula

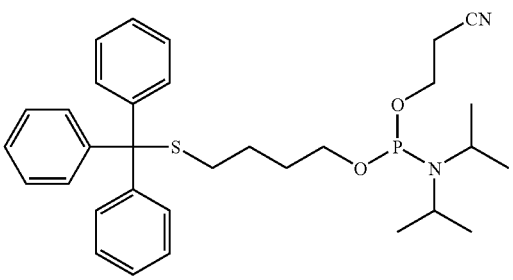 [SMILES: CC(C)N(C(C)C)P(OCCC#N)OCCCCSC(c1ccccc1)(c1ccccc1)c1ccccc1]

is provided.

In certain exemplary embodiments, Compound IV, having the formula

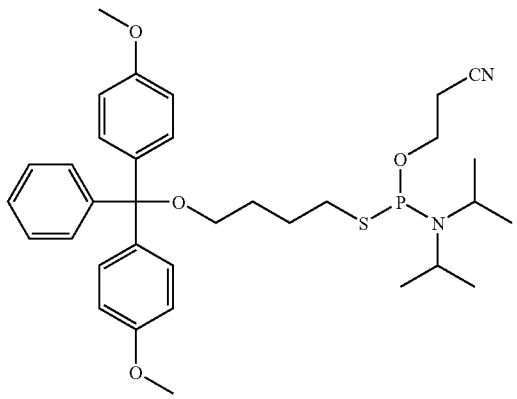 [SMILES: COc1ccc(C(OCCCCSP(OCCC#N)N(C(C)C)C(C)C)(c2ccccc2)c2ccc(OC)cc2)cc1]

is provided.

In certain exemplary embodiments, an oligonucleotide having attached to its 5' phosphate group and/or 3' hydroxyl group a linker selected from one or more of Compound II, Compound III and Compound IV is provided. In certain aspects, the linker is further attached to a fluorophore, biotin, a thiol, an amine, an aldehyde, a ketone, an epoxide, a solid support or a semi-solid support.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

DETAILED DESCRIPTION

The principles of the present invention may be applied with particular advantage to determine the identity of oligonucleotide sequences.

The present invention is based on part on the discovery of a novel class of cleavable phosphoramidite linkers (e.g., phosphoramidite 1 linkers) which, when incorporated into an oligonucleotide (e.g., via standard, solid-phase oligonucleotide synthesis), allows chemical removal of the cleavable linker and any moiety optionally attached to the linker from the oligonucleotide. The present invention is further based in part on the discovery of a novel method for using existing phosphoramidites (e.g., phosphoramidite 2 linkers) which, when incorporated into an oligonucleotide (e.g., via a modified solid-phase oligonucleotide synthesis scheme), allow chemical removal of the cleavable linker and any moiety attached to the linker from the oligonucleotide, and provide the oligonucleotide with a phosphate moiety at its 5' and/or 3' end.

As used herein, the term "cleavable linker" includes, but is not limited to linkers that can bind to a nucleotide and/or an oligonucleotide at either one or both of the 5' and the 3' ends of the nucleotide and/or oligonucleotide, and which can subsequently be cleaved from the nucleotide and/or oligonucleotide via contact with one or more chemicals described herein (e.g., $AgNO_3$, $I_2$ and the like). In certain aspects, a cleavable linker comprises an aliphatic and/or non-nucleoside based backbone that is less than 100, 90, 80, 70, 60, 50, 40 or 30 carbons in length. In certain exemplary embodiments, the aliphatic and/or non-nucleoside based backbone is between 2 and 24 carbons in length. The cleavable linker may optionally include one or more amide groups, ether groups, ketone groups or ester groups. Cleavable linkers include phosphoramidite linkers. Suitable phosphoramidite linkers include the novel phosphoramidite 1 linkers described herein, as well as phosphoramidite 2 linkers that are known in the art.

Figure 1:
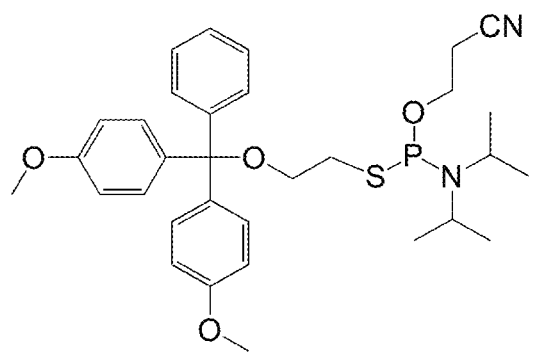
FIGS. 1A-1C depict examples of phosphoramidite 1 linkers. A depicts Compound II; B depicts Compound III; C depicts Compound IV.
Figure 1:
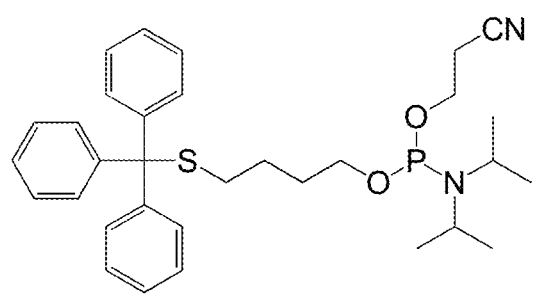
Figure 1:
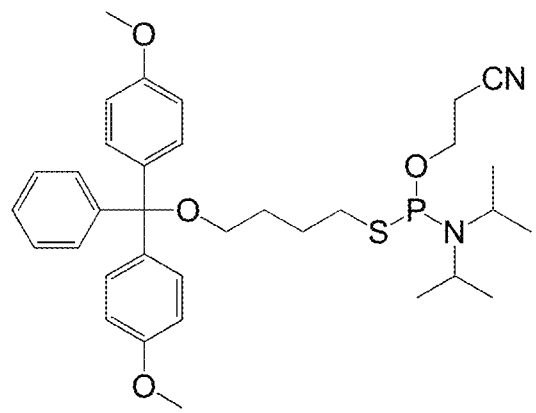

As used herein, a phosphoramidite 1 linker refers, but is not limited to, to an aliphatic and/or other non-nucleoside based linker. In certain exemplary embodiments, a phosphoramidite 1 linker includes a dimethoxytrityl protected oxygen and a sulfur phosphoramidite. Examples of three phosphoramidite 1 linkers are depicted in FIGS. 1A-1C. In certain exemplary embodiments, the linker backbone will contain between 2 and 24 carbons in length, and optionally may include one or more amide, ether, ketone and/or ester moieties.

Figure 2:
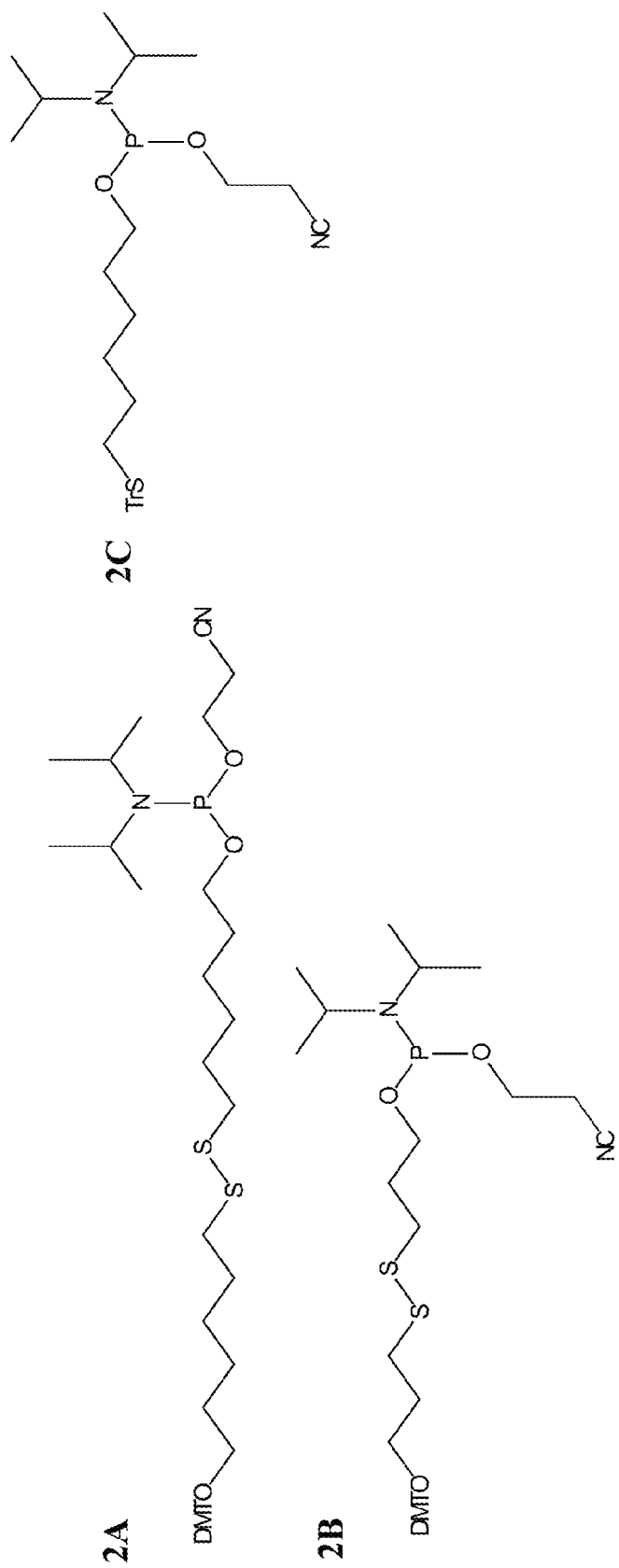
FIGS. 2A-2C depict commercially available versions of phosphoramidite 2. A is a C6 disulfide phosphoramidite; B is a C3 disulfide phosphoramidite; C is a C3 mercapto-trityl phosphoramidite. Tr=trityl.
Figure 3:
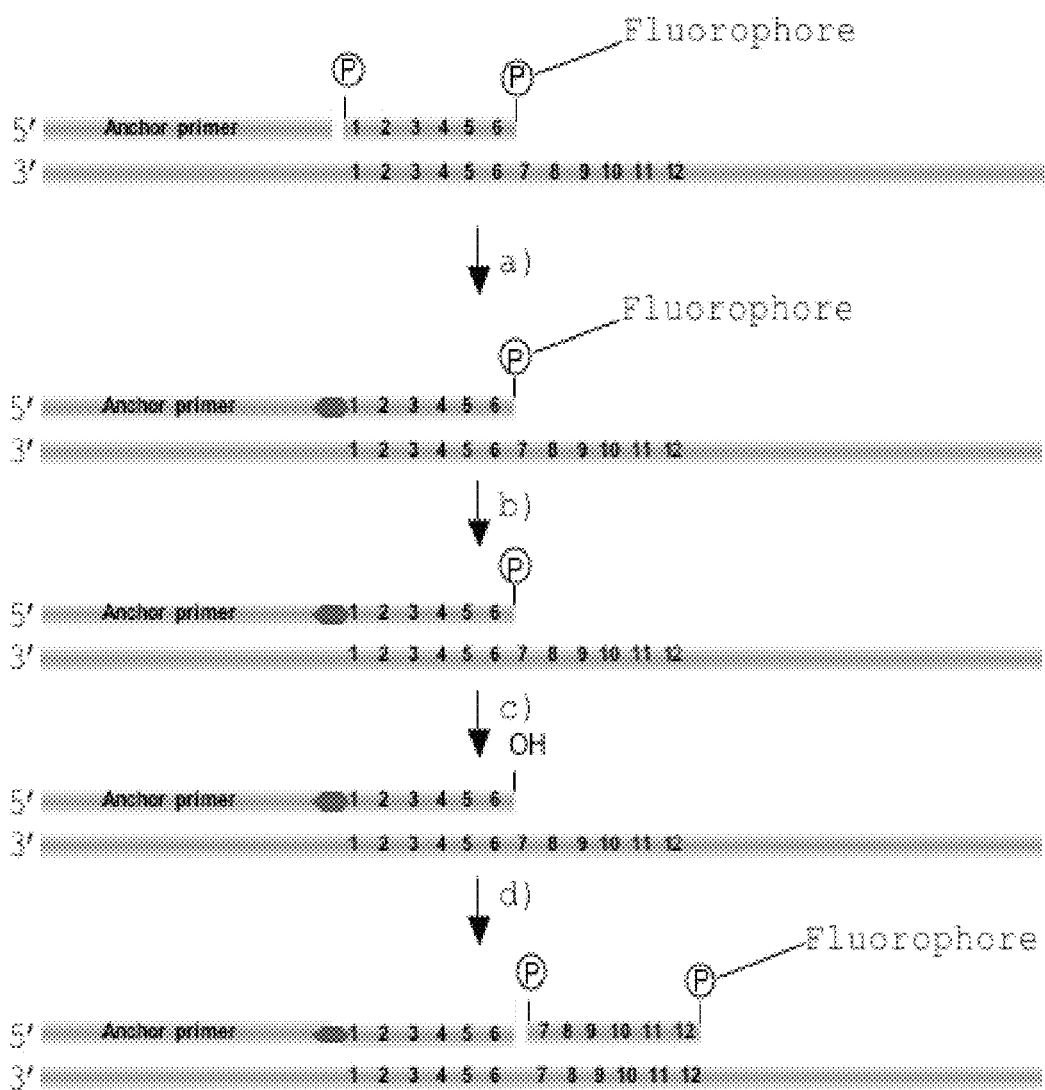
FIG. 3 depicts a 5'-3' sequencing reaction.
Figure 4:
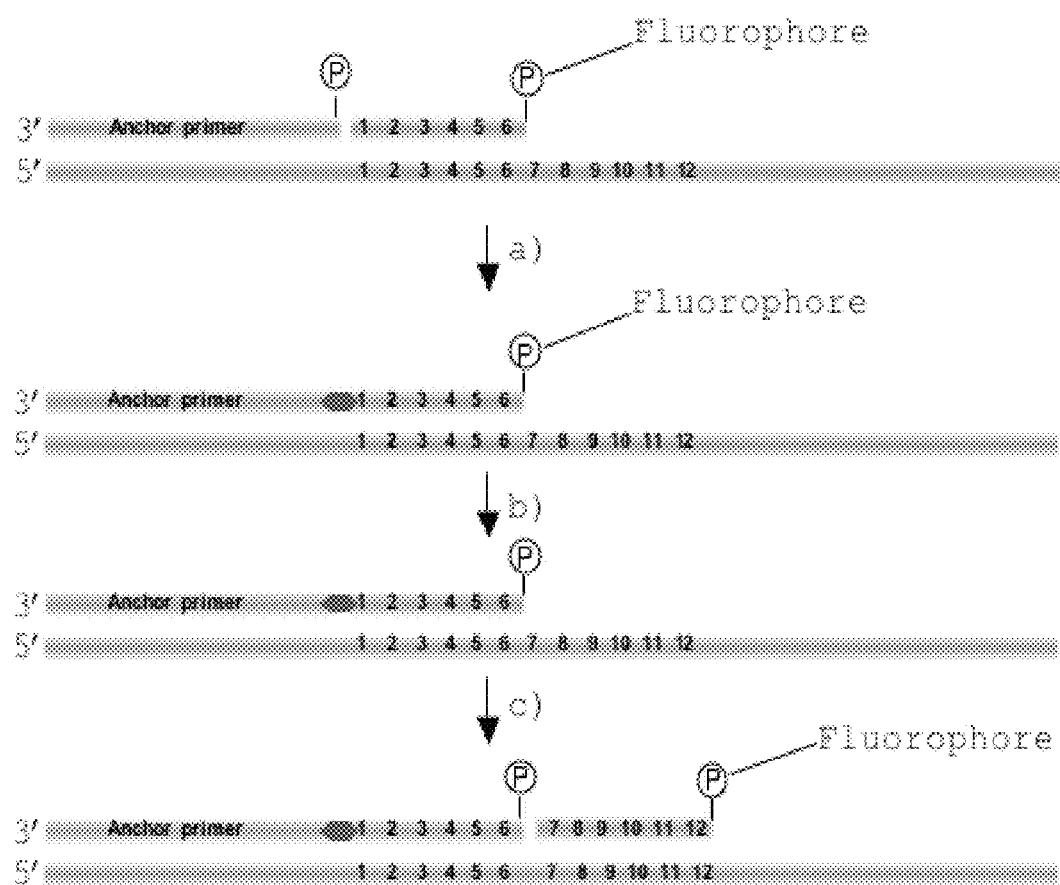
FIG. 4 depicts a 3'-5' sequencing reaction.

As used herein, a phosphoramidite 2 linker refers, but is not limited to, any aliphatic and/or non-nucleoside based phosphoramidite linker that is commercially available. Phosphoramidite 2 linkers are typically used to introduce a thiol functionality onto the 5' and/or 3' end of an oligonucleotide. FIGS. 2A-2C depict three examples of phosphoramidite 2 compounds that are commercially available.

The phosphoramidite linkers described herein (e.g., phosphoramidites 1, 2 and the like) are useful in methods for cleaving one or more modifications from a nucleotide and/or oligonucleotide (e.g., using one or more phosphoramidite 1 or 2 linkers); methods for reversibly blocking the reactivity of a 5' phosphate on an oligonucleotide (e.g., using phosphoramidite 1); methods to chemically cleave a 5' modification from an oligonucleotide and release an oligonucleotide with a 5' phosphate (e.g., using phosphoramidite 1); and in methods for increasing the read-length of multiplexed DNA sequencing by ligation (e.g., using one or more phosphoramidite 1 or 2 linkers).

As used herein, the term "chemical cleavage" refers, but is not limited to, the cleavage of one or more phosphoramidite linkers from one or more nucleotides and/or oligonucleotides by contacting the one or more phosphoramidite linkers with one or more suitable chemicals. As used herein, the term "suitable chemical" refers, but is not limited to, a chemical that can cleave a bridged-phosphorothioate linkage and can remove a phosphoramidite linker from a nucleotide and/or oligonucleotide, leaving a free phosphate group on the nucleotide and/or oligonucleotide at the cleavage site. Suitable chemicals include, but are not limited to $AgNO_3$, $AgCH_3COO$, $AgBrO_3$, $Ag_2SO_4$, or any compound that delivers $Ag^{2+}$, $HgCl_2$, $I_2$, $Br_2$, $I^-$, $Br^-$ and the like.

As used herein, the terms "nucleic acid molecule", "nucleic acid sequence", "nucleic acid fragment", "oligonucleotide" and "polynucleotide" are used interchangeably and are intended to include, but not limited to, a polymeric form of nucleotides that may have various lengths, either deoxyribonucleotides or ribonucleotides, or analogs thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Oligonucleotides useful in the methods described herein may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

In accordance with certain examples, methods of sequencing nucleic acid sequences by hybridization using one or more of the phosphoramidite linkers (e.g., phosphoramidite 1 and/or 2) linkers and/or the sequencing methods (e.g., sequencing by ligation (SbL) methods) described herein are provided. SbL generates DNA by measuring the serial ligation of an oligonucleotide (See, e.g., Applied Biosystems SOLiD™ System). Oligonucleotide probes having a detectable label are present simultaneously and compete for hybridization to one or more reference oligonucleotides. After each ligation, the detectable label is measured and subsequently cleaved before another round of ligation takes place. General sequencing methods are described in the art, such as sequencing by extension with reversible terminators, fluorescent in situ sequencing (FISSEQ), pyrosequencing, massively parallel signature sequencing (MPSS), solid sequencing (Applied Biosystems, Foster city, CA), and the like (described in Shendure et al. (2004) *Nat. Rev.* 5:335; reversible termination methods: U.S. Pat. Nos. 5,750,341 and 6,306,597; FISSEQ: Mitra et al. (2003) *Anal. Biochem.* 320:55; Pyrosequencing:

Ronaghi et al. (1998) *Science* 281:363; MPSS: Brenner et al. (2000) *Nat. Biotech.* 18:630), are suitable for use with the phosphoramidite linkers and assays described herein.

Oligonucleotide sequences may be isolated from natural sources or purchased from commercial sources. In certain exemplary embodiments, oligonucleotide sequences may be prepared using one or more of the phosphoramidite linkers and/or the SbL methods described herein. Oligonucleotide sequences may also be prepared by any suitable method, e.g., standard phosphoramidite methods such as those described herein below as well as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain exemplary embodiments, oligonucleotide sequences may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) *Proc. Natl. Acad. Sci. U.S.A.* 93:13555; *Synthetic DNA Arrays* In Genetic Engineering, Vol. 20:111, Plenum Press (1998); Duggan et al. (1999) *Nat. Genet.* S21:10; *Microarrays: Making Them and Using Them* In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597.

In certain exemplary embodiments, one or more oligonucleotide sequences described herein are immobilized on a support (e.g., a solid and/or semi-solid support). In certain aspects, an oligonucleotide sequence can be attached to a support using one or more of the phosphoramidite linkers described herein. Suitable supports include, but are not limited to, slides, beads, chips, particles, strands, gels, sheets, tubing, spheres, containers, capillaries, pads, slices, films, plates and the like. In various embodiments, a solid support may be biological, nonbiological, organic, inorganic, or any combination thereof. When using a support that is substantially planar, the support may be physically separated into regions, for example, with trenches, grooves, wells, or chemical barriers (e.g., hydrophobic coatings, etc.).

In certain exemplary embodiments, a support is a microarray. As used herein, the term "microarray" refers in one embodiment to a type of assay that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate creates a substantially planar surface. Spatially defined sites may additionally be "addressable" in that its location and the identity of the immobilized probe at that location are known or determinable.

Oligonucleotides immobilized on microarrays include nucleic acids that are generated in or from an assay reaction. Typically, the oligonucleotides or polynucleotides on microarrays are single stranded and are covalently attached to the solid phase support, usually by a 5'-end or a 3'-end. In certain exemplary embodiments, probes are immobilized via one or more of the cleavable linkers described herein. The density of non-overlapping regions containing nucleic acids in a microarray is typically greater than 100 per $cm^2$, and more typically, greater than 1000 per $cm^2$. Microarray technology relating to nucleic acid probes is reviewed in the following exemplary references: Schena, Editor, *Microarrays: A Practical Approach* (IRL Press, Oxford, 2000); Southern, *Current Opin. Chem. Biol.*, 2: 404-410 (1998); *Nature Genetics* Supplement, 21:1-60 (1999); and Fodor et al, U.S. Pat. Nos. 5,424,186; 5,445,934; and 5,744,305.

Methods of immobilizing oligonucleotides to a support are known in the art (beads: Dressman et al. (2003) *Proc. Natl. Acad. Sci. USA* 100:8817, Brenner et al. (2000) *Nat. Biotech.* 18:630, Albretsen et al. (1990) *Anal. Biochem.* 189:40, and Lang et al. *Nucleic Acids Res.* (1988) 16:10861; nitrocellulose: Ranki et al. (1983) *Gene* 21:77; cellulose: Goldkorn (1986) *Nucleic Acids Res.* 14:9171; polystyrene: Ruth et al. (1987) Conference of Therapeutic and Diagnostic Applications of Synthetic Nucleic Acids, Cambridge U.K.; teflon-acrylamide: Duncan et al. (1988) *Anal. Biochem.* 169:104; polypropylene: Polsky-Cynkin et al. (1985) *Clin. Chem.* 31:1438; nylon: Van Ness et al. (1991) *Nucleic Acids Res.* 19:3345; agarose: Polsky-Cynkin et al., *Clin. Chem.* (1985) 31:1438; and sephacryl: Langdale et al. (1985) *Gene* 36:201; latex: Wolf et al. (1987) *Nucleic Acids Res.* 15:2911).

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell*, 3d edition, Garland Publishing, 1994.

In certain exemplary embodiments, a detectable label can be used to detect one or more nucleotides and/or oligonucleotides described herein. Examples of detectable markers include various radioactive moieties, enzymes, prosthetic groups, fluorescent markers, luminescent markers, bioluminescent markers, metal particles, protein-protein binding pairs, protein-antibody binding pairs and the like. Examples of fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorimidases, phosphatases, peroxidases, cholinesterases and the like. Identifiable markers also include radioactive compounds such as $^{125}$I, $^{35}$S, $^{14}$C, or $^{3}$H. Identifiable markers are commercially available from a variety of sources.

Fluorescent labels and their attachment to nucleotides and/or oligonucleotides are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); and Wetmur, *Critical Reviews in Biochemistry and Molecular Biology*, 26:227-259 (1991). Particular methodologies applicable to the invention are disclosed in the following sample of references: U.S. Pat. Nos. 4,757,141, 5,151,507 and 5,091,519. In one aspect, one or more fluorescent dyes are used as labels for labeled target sequences, e.g., as disclosed by U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); Lee et al.; U.S. Pat. No. 5,066,580 (xanthine dyes); U.S. Pat. No. 5,688,648 (energy transfer dyes); and the like. Labelling can also be carried out with quantum dots, as disclosed in the following patents and patent publications: U.S. Pat. Nos. 6,322,901, 6,576,291, 6,423,551, 6,251,303, 6,319,426, 6,426,513, 6,444,143, 5,990,479, 6,207,392, 2002/0045045 and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

Commercially available fluorescent nucleotide analogues readily incorporated into nucleotide and/or oligonucleotide sequences include, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHODAMINE GREEN™-5-UTP, ALEXA FLUOR™ 488-5-UTP, LEXA FLUOR™ 546-14-UTP (Molecular Probes, Inc. Eugene, Oreg.) and the like. Protocols are known in the art for custom synthesis of nucleotides having other fluorophores (See, Henegariu et al. (2000) *Nature Biotechnol.* 18:345).

Other fluorophores available for post-synthetic attachment include, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, Cy7 (Amersham Biosciences, Piscataway, N.J.) and the like. FRET tandem fluorophores may also be used, including, but not limited to, PerCP-Cy5.5, PE-Cy5, PE-Cy5.5, PE-Cy7, PE-Texas Red, APC-Cy7, PE-Alexa dyes (610, 647, 680), APC-Alexa dyes and the like.

Metallic silver or gold particles may be used to enhance signal from fluorescently labeled nucleotide and/or oligonucleotide sequences (Lakowicz et al. (2003) *Bio Techniques* 34:62).

Biotin, or a derivative thereof, may also be used as a label on a nucleotide and/or an oligonucleotide sequence, and subsequently bound by a detectably labeled avidin/streptavidin derivative (e.g. phycoerythrin-conjugated streptavidin), or a detectably labeled anti-biotin antibody. Digoxigenin may be incorporated as a label and subsequently bound by a detectably labeled anti-digoxigenin antibody (e.g. fluoresceinated anti-digoxigenin). An aminoallyl-dUTP residue may be incorporated into an oligonucleotide sequence and subsequently coupled to an N-hydroxy succinimide (NHS) derivatized fluorescent dye. In general, any member of a conjugate pair may be incorporated into a detection oligonucleotide provided that a detectably labeled conjugate partner can be bound to permit detection. As used herein, the term antibody refers to an antibody molecule of any class, or any sub-fragment thereof, such as an Fab.

Other suitable labels for an oligonucleotide sequence may include fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr) and the like. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM.

In certain exemplary embodiments, a nucleotide and/or an oligonucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, PCT publication WO 91/17160 and the like. Many different hapten-capture agent pairs are available for use. Exemplary haptens include, but are not limited to, biotin, des-biotin and other derivatives, dinitrophenol, dansyl, fluorescein, CY5, digoxigenin and the like. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In certain exemplary embodiments, a first (e.g., probe) oligonucleotide sequence is annealed to a second (e.g., reference) oligonucleotide sequence. The terms "annealing" and "hybridization", as used herein, are used interchangeably to mean the formation of a stable duplex. In one aspect, stable duplex means that a duplex structure is not destroyed by a stringent wash, e.g., conditions including temperature of about 5° C. less that the $T_m$ of a strand of the duplex and low monovalent salt concentration, e.g., less than 0.2 M, or less than 0.1 M. The term "perfectly matched", when used in reference to a duplex means that the polynucleotide and/or oligonucleotide strands making up the duplex form a double stranded structure with one another such that every nucleotide in each strand undergoes Watson-Crick base pairing with a nucleotide in the other strand. The term "duplex" includes, but is not limited to, the pairing of nucleoside analogs, such as deoxyinosine, nucleosides with 2-aminopurine bases, PNAs, and the like, that may be employed. A "mismatch" in a duplex between two oligonucleotides means that a pair of nucleotides in the duplex fails to undergo Watson-Crick bonding.

As used herein, the term "hybridization conditions", will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, e.g., conditions under which a probe will specifically hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual*, 2nd Ed. Cold Spring Harbor Press (1989) and Anderson *Nucleic Acid Hybridization*, $1^{st}$ Ed., BIOS Scientific Publishers Limited (1999). As used herein, the terms "hybridizing specifically to" or "specifically hybridizing to" or similar terms refer to the binding, duplexing, or hybridizing of a molecule substantially to a particular nucleotide sequence or sequences under stringent conditions.

As used herein, the term "hybridization-based assay" is intended to refer to an assay that relies on the formation of a stable complex as the result of a specific binding event. In one aspect, a hybridization-based assay means any assay that relies on the formation of a stable duplex or triplex between a probe and a target nucleotide sequence for detecting or measuring such a sequence. A "probe" in reference to a hybridization-based assay refers to an oligonucleotide sequence that has a sequence that is capable of forming a stable hybrid (or triplex) with its complement in a target nucleic acid and that is capable of being detected, either directly or indirectly.

The following examples are set forth as being representative of the present invention. These examples are not to be construed as limiting the scope of the invention as these and other equivalent embodiments will be apparent in view of the present disclosure, figures, tables, and accompanying claims. The contents of all references, patents and published patent applications cited throughout this application are hereby incorporated by reference in their entirety for all purposes.

EXAMPLE I

Synthesis and Use of Phosphoramidite 1

Phosphoramidite 1 is comprised of an aliphatic or other non-nucleoside based linker with a dimethoxytrityl protected oxygen and a sulfur phosphoramidite. Examples are depicted in FIGS. 1A-1C. In general, the linker backbone will contain between 2 and 24 carbons in length, may or may not include amides, ethers, ketones or esters. Phosphoramidite 1 can be used as a chemically reversible blocking group for a 5' phosphate, a 3' OH and/or to cleave a modification from an oligonucleotide and release an oligonucleotide having a phosphate group at one or both of the 5' end and the 3' end.

Synthetic Routes to Phosphoramidite 1

Phosphoramidite 1 can be easily synthesized by the following general protocols:

1. Via a symmetric disulfide.

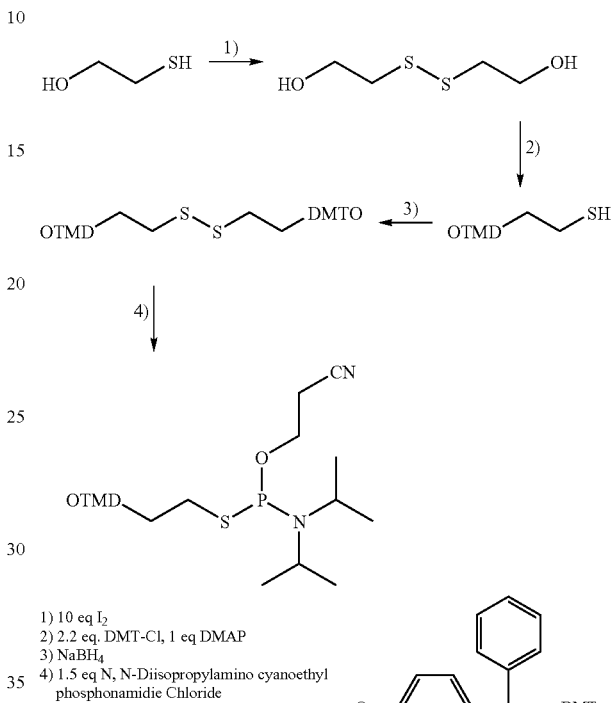

1) 10 eq I$_2$
2) 2.2 eq. DMT-Cl, 1 eq DMAP
3) NaBH$_4$
4) 1.5 eq N, N-Diisopropylamino cyanoethyl phosphonamidie Chloride

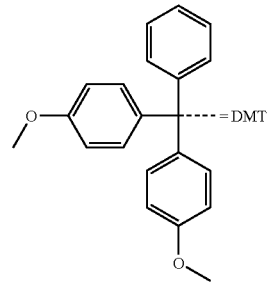

2. Via selective deprotection of a thio-dimethoxytrityl.

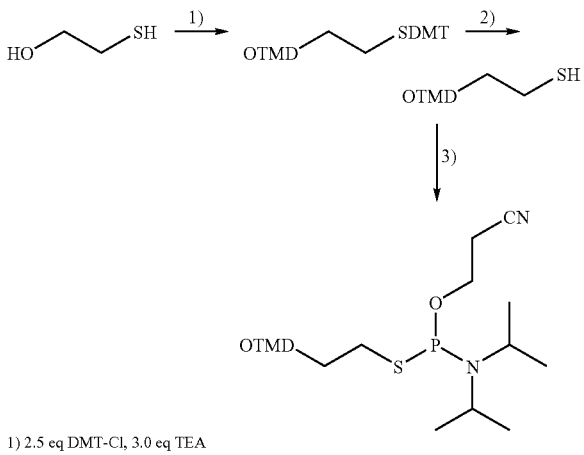

1) 2.5 eq DMT-Cl, 3.0 eq TEA
2) AgNO$_3$, DTT or NaBH$_2$
3) 1.5 eq N, N-Diisopropylamino cyanoethyl phosphonamidie Chloride 3. Via selective protection of the thiol with a group that is not dimethoxytrityl.

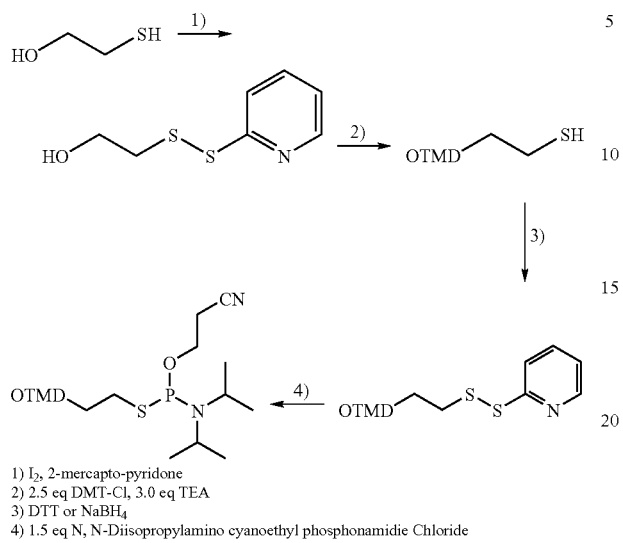

1) I₂, 2-mercapto-pyridone
2) 2.5 eq DMT-Cl, 3.0 eq TEA
3) DTT or NaBH₄
4) 1.5 eq N, N-Diisopropylamino cyanoethyl phosphonamidie Chloride Synthesis of Oligonucleotides Containing Phosphoramidite 1

Oligonucleotides containing phosphoramidite 1 can be synthesized using standard phosphoramidite chemistry as described further herein. Following incorporation of phosphoramidite 1 into the oligonucleotide, another phosphoramidite may or may not be added.

Use of Phosphoramidite 1 as a Chemically Reversible Blocking Group for a 5' Phosphate Incorporation of phosphoramidite 1 into an oligonucleotide will block the 5' phosphate, rendering the oligonucleotide inert to chemical and biochemical processes that require a 5' phosphate. Importantly, this linker should not affect the hybridization specificity of the oligonucleotide. The blocked 5' phosphate contains a bridged-phosphorothioate linkage that is readily cleaved by chemical methods which include, but are not limited to, aqueous AgNO₃ and/or I₂. Upon cleavage, the linker will be released and a 5' phosphate will be present on the oligonucleotide as shown below (the following reaction scheme illustrates cleavage of the 5' phosphate protecting group with AgNO₃).

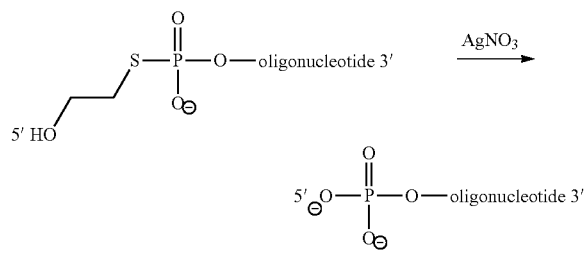

Use of Phosphoramidite 1 to Cleave a Modification from an Oligonucleotide and Release an Oligonucleotide with a 5' Phosphate Incorporation of phosphoramidite 1 onto the 5' end of an oligonucleotide between the oligonucleotide and a modification, including but not limited to a biotin, thiol, amine, aldehyde, ketone, epoxide, solid support, surface, fluorophore or any of the detectable labels described herein, allows release of the oligonucleotide from the modification in such a manner that a 5' phosphate is generated on the oligonucleotide as shown below (the following reaction scheme illustrates cleavage of a functional group (e.g., biotin, etc.) from the 5' end of an oligonucleotide). Importantly, this linker should not affect the hybridization specificity of the oligonucleotide.

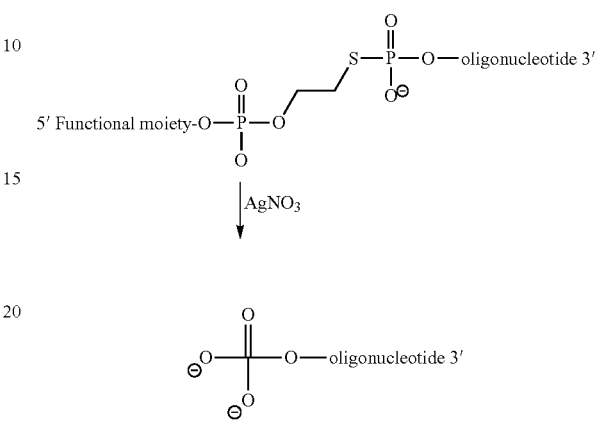

Art-known methods include the use of disulfides or photocleavable moieties to cleave a functionality from an oligonucleotide. The reduction of disulfide containing linkers for release of a functionality does not generate a 5' phosphate, however. Furthermore, the use of photocleavable linkers requires that the photocleavable moiety be proximal to the oligonucleotide and can thus affect oligonucleotide hybridization prior to cleavage. In addition, the large amounts of energy required to activate photo-cleavage can damage the DNA.

EXAMPLE II

Phosphoramidite 2

Phosphoramidites 2a, 2b, and 2c (FIG. 2) are commercially available and are typically used to introduce a thiol functionality onto the 5' or 3' end of an oligonucleotide. By a modification of the oligonucleotide synthesis protocol, phosphoramidites 2a, 2b, or 2c can be used to create a chemically cleavable linker between the 3' end of an oligonucleotide and a functional moiety.

Synthesis of Oligonucleotides Containing Phosphoramidite 2

An alternative oligonucleotide synthesis scheme using a cleavable phosphoramidite 2 linker between an oligonucleotide and a 3' modification is shown below. The procedure involves reduction of the disulfide with DTT, NaBH₄, or TCEP during oligonucleotide synthesis for 2a and 2b (step 3). For 2c, the generation of the free thiol occurs after treatment with AgNO₃ and subsequent thiol exchange with DTT. In standard oligonucleotide synthesis, a dimethoxytrityl protecting group is removed from the 5' OH of the growing strand. This 5' OH functionality acts as the nucleophile in a reaction with the next phosphoramidite added to the synthesis. In this scheme, the reduction of the disulfide (or AgNO₃, DTT treatment for 2c) generates a free thiol that acts as the nucleophile in a reaction with the next phosphoramidite added to the synthesis (the following reaction scheme illustrates generating a 5' thiol after coupling 2b to a modification).

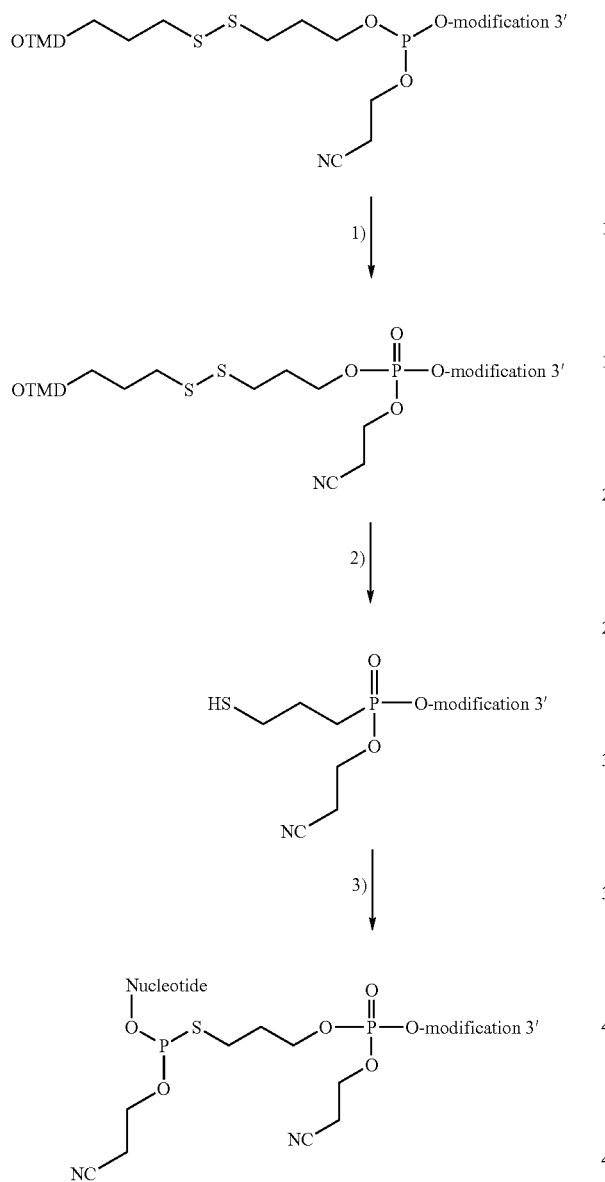

1) oxidation with I₂; standard practice
2) reduction with DTT; nonstandard practice
3) addition of next nucleoside phosphoramidite; standard practice Use of Phosphoramidite 2 to Cleave a Modification from an Oligonucleotide Using the synthesis strategy outlined above, incorporation of 2a, 2b, or 2c onto the 3' end of an oligonucleotide between the oligonucleotide and an optional modification, including but not limited to a biotin, thiol, amine, aldehyde, ketone, epoxide, solid support, surface, fluorophore, or any of the detectable labels described herein, allows release of the oligonucleotide from the modification in such a manner that a 3' phosphate is generated on the oligonucleotide as shown below (the following reaction scheme illustrates cleavage of a functional group (e.g., biotin and the like) from the 3' end of an oligonucleotide). Importantly, this linker should not affect the hybridization specificity of the oligonucleotide.

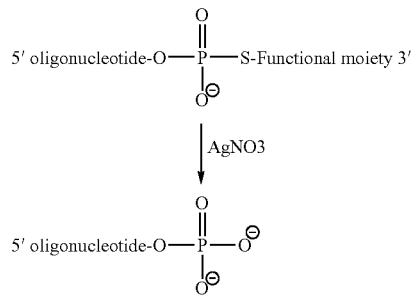

EXAMPLE III

5'-3' Sequencing and Sequencing by Ligation (SBL)

Phosphoramidite 2 can be used to increase the read-length of multiplexed DNA sequencing by ligation.

5'-3' Sequencing

The following phosphoramidite 2 linker will be synthesized.

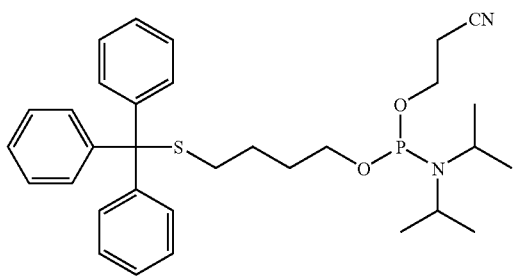 [SMILES: CC(C)N(C(C)C)P(OCCC#N)OCCCCSC(c1ccccc1)(c1ccccc1)c1ccccc1]

During probe synthesis, the oligonucleotide will be synthesized in the following manner: 3'-fluorophore-linker-XXXXXX-phosphate-5', where X=N or defined A, G, T or C. The synthesis will result in a probe of structure (5'-3' direction; notable bonds visible):

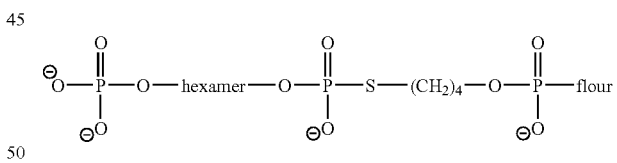

SbL Protocol

1. Ligation: ligation of 5'-phosphorylated probes to ribonucleotide (rN) terminated anchor primer.
2. Capping: oxidation of 3' vicinal-diol of unligated anchor-primer with NaIO₄ cleavage. AgNO₃ will quantitatively cleave the bridged-phosphorothioate yielding a 3' phosphate subsequently removed with phosphatase.
3. 2$^{nd}$ ligation: ligation onto extended probe

EXAMPLE IV

3'-5' Sequencing and SBL

Phosphoramidite 1 can be used to increase the read-length of multiplexed DNA sequencing by ligation.

3'-5' Sequencing

The following phosphoramidite 1 linker will be synthesized.

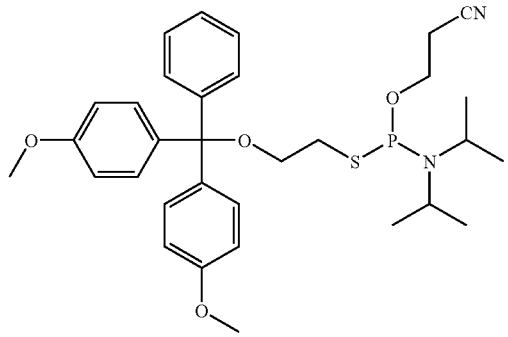 [SMILES: COc1ccc(C(OCCSP(OCCC#N)N(C(C)C)C(C)C)(c2ccccc2)c2ccc(OC)cc2)cc1]

During probe synthesis, the oligonucleotide will be synthesized in the following manner: 3'-XXXXXX-linker-fluorophore-5', where X=N or defined A, G, T or C. The synthesis will result in a probe of structure (5'-3' direction; notable bonds visible):

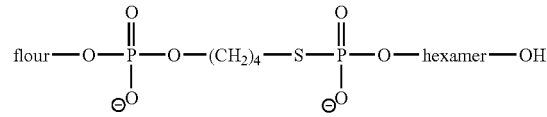

SbL Protocol

1. Ligation: ligation of probes to 5'-phosphorylated anchor-primer.
2. Capping: removal of unligated anchor-primer 5'-phosphate with phosphatase [note: 'capping' usually means putting something on to halt reactivity. Here we take something off to halt reactivity.]
3. Cleavage: $AgNO_3$ will quantitatively cleave the bridged-phosphorothioate yielding a 5' phosphate and removing the fluorophore.
4. $2^{nd}$ ligation: ligation onto extended probe.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

What is claimed is:

1. A method of determining a nucleotide sequence of a reference oligonucleotide comprising the steps of:
   a) providing a reference oligonucleotide;
   b) providing a probe oligonucleotide having a detectable label bound to its 5' phosphate group via a cleavable phosphoramidite 1 linker;
   c) allowing the probe oligonucleotide to hybridize to the reference oligonucleotide;
   d) detecting the detectable label; and
   e) chemically cleaving the cleavable linker to remove the detectable label and to allow the probe oligonucleotide to have a 5' phosphate group.
2. The method of claim 1, wherein the cleavable linker includes an aliphatic backbone.
3. The method of claim 2, wherein the aliphatic backbone is between 2 and 24 carbons in length.
4. The method of claim 2, wherein the aliphatic backbone comprises at least one amide group, ether group, ketone group or ester group.
5. The method of claim 1, wherein the phosphoramidite 1 linker is

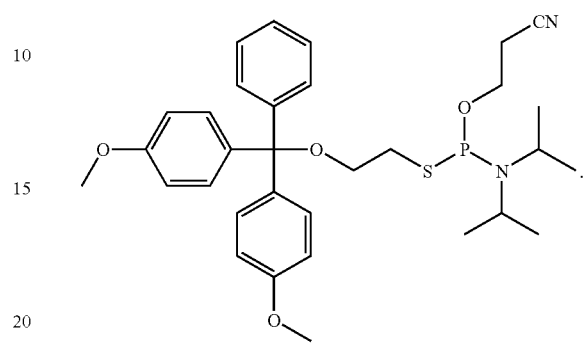

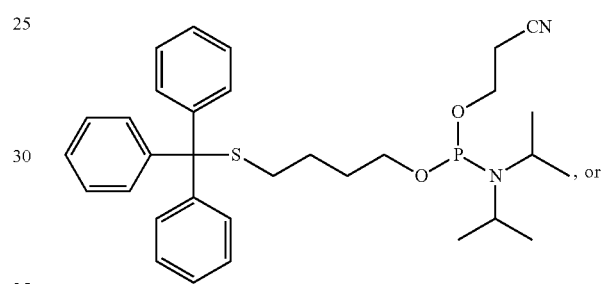

, or

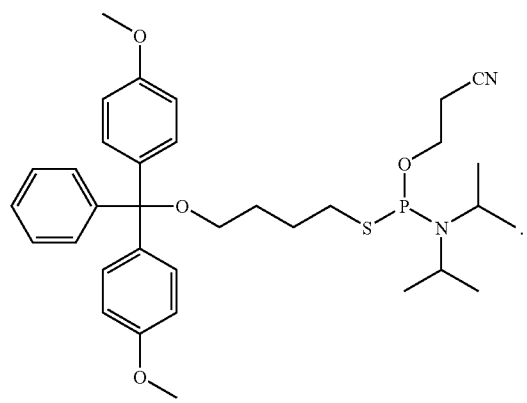

6. The method of claim 1, wherein the chemically cleaving step includes contacting the cleavable linker with one or more of $AgNO_3$ and $I_2$.

7. The method of claim 1, wherein the probe oligonucleotide contains the same number of nucleotides after chemically cleaving the cleavable linker as it contained prior to cleavage.

8. The method of claim 1, wherein the detectable label is a fluorophore.

9. The method of claim 1, wherein the probe oligonucleotide is a hexamer.

10. A method of determining a nucleotide sequence of a reference oligonucleotide comprising the steps of:
   a) providing a reference oligonucleotide;
   b) providing a probe oligonucleotide having a detectable label bound to its 3' end via a cleavable phosphoramidite 1 linker;
   c) allowing the probe oligonucleotide to hybridize to the reference oligonucleotide;
   d) detecting the detectable label; and
   e) chemically cleaving the cleavable linker to remove the detectable label to allow the probe oligonucleotide to have a 3' phosphate group.

11. The method of claim 10, wherein the cleavable linker includes an aliphatic backbone.

12. The method of claim 11, wherein the aliphatic backbone is between 2 and 24 carbons in length.

13. The method of claim 11, wherein the aliphatic backbone comprises at least one amide group, ether group, ketone group or ester group.

14. The method of claim 12, wherein the phosphoramidite 1 linker is

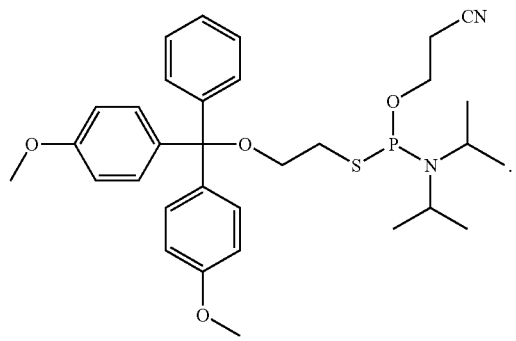 [SMILES: COc1ccc(C(OCCSP(OCCC#N)N(C(C)C)C(C)C)(c2ccccc2)c2ccc(OC)cc2)cc1 ; "."]

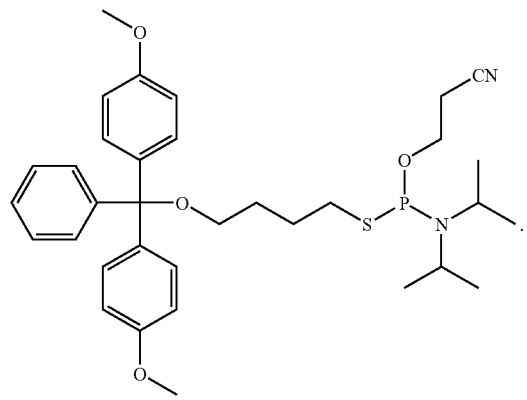 [SMILES: COc1ccc(C(OCCCCSP(OCCC#N)N(C(C)C)C(C)C)(c2ccccc2)c2ccc(OC)cc2)cc1 ; "."]

15. The method of claim 12, wherein the chemically cleaving step includes contacting the cleavable linker with one or more of $AgNO_3$ and $I_2$.

16. The method of claim 10, wherein the probe oligonucleotide contains the same number of nucleotides after chemically cleaving the cleavable linker as it contained prior to cleavage.

17. The method of claim 10, wherein the detectable label is a fluorophore.

18. The method of claim 10, wherein the probe oligonucleotide is a hexamer.

19. A method of determining a nucleotide sequence of a reference oligonucleotide comprising the steps of:
   a) providing a reference oligonucleotide;
   b) providing a probe oligonucleotide having a detectable label bound to its 5' phosphate group via a cleavable linker including an aliphatic backbone;
   c) allowing the probe oligonucleotide to hybridize to the reference oligonucleotide;
   d) detecting the detectable label; and
   e) chemically cleaving the cleavable linker to remove the detectable label and to allow the probe oligonucleotide to have a 5' phosphate group, wherein the chemically cleaving step includes contacting the cleavable linker with one or more of $AgNO_3$ and $I_2$.

20. The method of claim 19, wherein the aliphatic backbone is between 2 and 24 carbons in length.

21. The method of claim 19, wherein the aliphatic backbone comprises at least one amide group, ether group, ketone group or ester group.

22. A method of determining a nucleotide sequence of a reference oligonucleotide comprising the steps of:
   a) providing a reference oligonucleotide;
   b) providing a probe oligonucleotide having a detectable label bound to its 5' phosphate group via a cleavable linker;
   c) allowing the probe oligonucleotide to hybridize to the reference oligonucleotide;
   d) detecting the detectable label; and
   e) chemically cleaving the cleavable linker to remove the detectable label and to allow the probe oligonucleotide to have a 5' phosphate group, wherein the chemically cleaving step includes contacting the cleavable linker with one or more of $AgNO_3$ and $I_2$ and wherein the cleavable linker is a phosphoramidite linker.

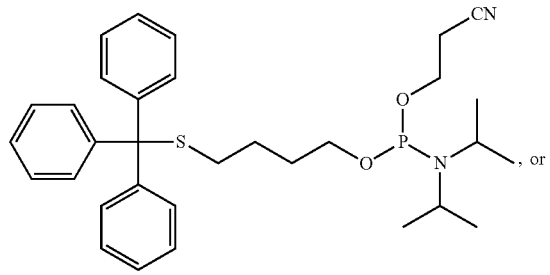 [SMILES: CC(C)N(C(C)C)P(OCCC#N)OCCCCSC(c1ccccc1)(c1ccccc1)c1ccccc1 ; ","], or

23. The method of claim 22, wherein the cleavable linker is a phosphoramidite 1 linker.

24. The method of claim 22, wherein the cleavable linker is

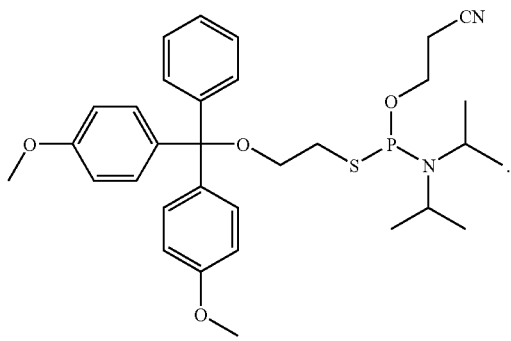 [SMILES: COc1ccc(C(OCCSP(OCCC#N)N(C(C)C)C(C)C)(c2ccccc2)c2ccc(OC)cc2)cc1 ; "."]

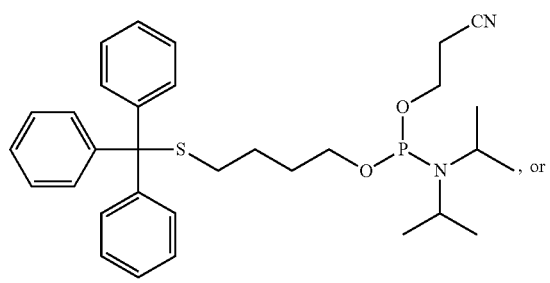 [SMILES: CC(C)N(C(C)C)P(OCCC#N)OCCCCSC(c1ccccc1)(c1ccccc1)c1ccccc1 ; ","], or

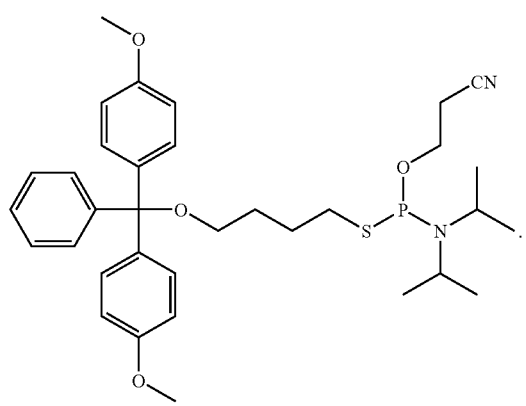 [SMILES: COc1ccc(C(OCCCCSP(OCCC#N)N(C(C)C)C(C)C)(c2ccccc2)c2ccc(OC)cc2)cc1 ; "."]

25. A method of determining a nucleotide sequence of a reference oligonucleotide comprising the steps of:
a) providing a reference oligonucleotide;
b) providing a probe oligonucleotide having a detectable label bound to its 5' phosphate group via a cleavable linker having an aliphatic backbone;
c) allowing the probe oligonucleotide to hybridize to the reference oligonucleotide;
d) detecting the detectable label; and
e) chemically cleaving the cleavable linker to remove the detectable label and to allow the probe oligonucleotide to have a 5' phosphate group, wherein the chemically cleaving step includes contacting the cleavable linker with one or more of $AgNO_3$ and $I_2$ and wherein the probe oligonucleotide contains the same number of nucleotides after chemically cleaving the cleavable linker as it contained prior to cleavage.

26. A method of determining a nucleotide sequence of a reference oligonucleotide comprising the steps of:
a) providing a reference oligonucleotide;
b) providing a probe oligonucleotide having a detectable label bound to its 5' phosphate group via a cleavable linker having an aliphatic backbone;
c) allowing the probe oligonucleotide to hybridize to the reference oligonucleotide;
d) detecting the detectable label; and
e) chemically cleaving the cleavable linker to remove the detectable label and to allow the probe oligonucleotide to have a 5' phosphate group, wherein the chemically cleaving step includes contacting the cleavable linker with one or more of $AgNO_3$ and $I_2$ and wherein the detectable label is a fluorophore.

27. The method of claim 19 wherein the probe oligonucleotide is a hexamer.

28. A method of determining a nucleotide sequence of a reference oligonucleotide comprising the steps of:
a) providing a reference oligonucleotide;
b) providing a probe oligonucleotide having a detectable label bound to its 5' phosphate group via a cleavable linker including an aliphatic backbone;
c) allowing the probe oligonucleotide to hybridize to the reference oligonucleotide;
d) detecting the detectable label; and
e) chemically cleaving the cleavable linker to remove the detectable label and to allow the probe oligonucleotide to have a 3' phosphate group, wherein the chemically cleaving step includes contacting the cleavable linker with one or more of $AgNO_3$ and $I_2$.

29. The method of claim 28, wherein the aliphatic backbone is between 2 and 24 carbons in length.

30. The method of claim 28, wherein the aliphatic backbone comprises at least one amide group, ether group, ketone group or ester group.

31. A method of determining a nucleotide sequence of a reference oligonucleotide comprising the steps of:
a) providing a reference oligonucleotide;
b) providing a probe oligonucleotide having a detectable label bound to its 5' phosphate group via a cleavable linker;
c) allowing the probe oligonucleotide to hybridize to the reference oligonucleotide;
d) detecting the detectable label; and
e) chemically cleaving the cleavable linker to remove the detectable label and to allow the probe oligonucleotide to have a 3' phosphate group, wherein the chemically cleaving step includes contacting the cleavable linker with one or more of $AgNO_3$ and $I_2$ and wherein the cleavable linker is a phosphoramidite linker.

32. The method of claim 31, wherein the cleavable linker is a phosphoramidite 1 linker.

33. The method of claim 31, wherein the cleavable linker is

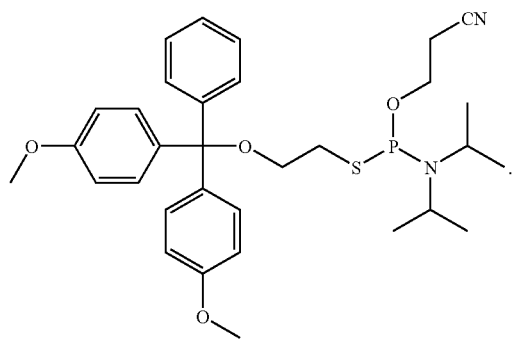 [SMILES: COc1ccc(C(OCCSP(OCCC#N)N(C(C)C)C(C)C)(c2ccccc2)c2ccc(OC)cc2)cc1 ; "."]

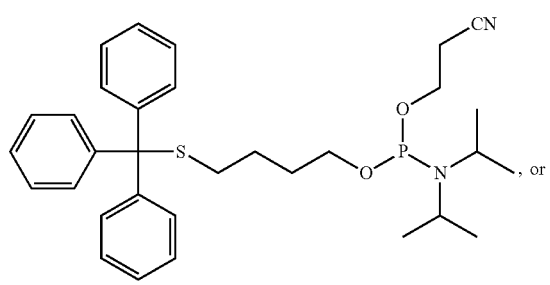 [SMILES: CC(C)N(C(C)C)P(OCCC#N)OCCCCSC(c1ccccc1)(c1ccccc1)c1ccccc1 ; ","]

, or

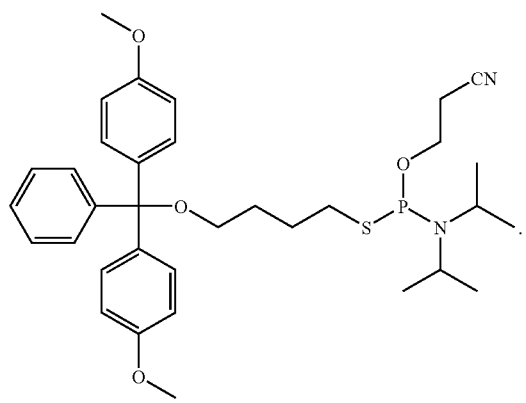 [SMILES: COc1ccc(C(OCCCCSP(OCCC#N)N(C(C)C)C(C)C)(c2ccccc2)c2ccc(OC)cc2)cc1 ; "."]

34. A method of determining a nucleotide sequence of a reference oligonucleotide comprising the steps of:
   a) providing a reference oligonucleotide;
   b) providing a probe oligonucleotide having a detectable label bound to its 5' phosphate group via a cleavable linker;
   c) allowing the probe oligonucleotide to hybridize to the reference oligonucleotide;
   d) detecting the detectable label; and
   e) chemically cleaving the cleavable linker to remove the detectable label and to allow the probe oligonucleotide to have a 3' phosphate group, wherein the chemically cleaving step includes contacting the cleavable linker with one or more of $AgNO_3$ and $I_2$ and wherein the probe oligonucleotide contains the same number of nucleotides after chemically cleaving the cleavable linker as it contained prior to cleavage.

35. The method of claim 28 wherein the detectable label is a fluorophore.

36. The method of claim 28, wherein the probe oligonucleotide is a hexamer.

37. A method of determining a nucleotide sequence of a reference oligonucleotide comprising the steps of:
   a) providing a reference oligonucleotide;
   b) providing a probe oligonucleotide having a detectable label bound to its 5' phosphate group via a cleavable linker including an aliphatic backbone;
   c) allowing the probe oligonucleotide to hybridize to the reference oligonucleotide;
   d) detecting the detectable label; and
   e) chemically cleaving the cleavable linker to remove the detectable label and to allow the probe oligonucleotide to have a 5' phosphate group, wherein the probe oligonucleotide contains the same number of nucleotides after chemically cleaving the cleavable linker as it contained prior to cleavage.

38. The method of claim 37, wherein the aliphatic backbone is between 2 and 24 carbons in length.

39. The method of claim 37, wherein the aliphatic backbone comprises at least one amide group, ether group, ketone group or ester group.

40. A method of determining a nucleotide sequence of a reference oligonucleotide comprising the steps of:
   a) providing a reference oligonucleotide;
   b) providing a probe oligonucleotide having a detectable label bound to its 5' phosphate group via a cleavable linker;
   c) allowing the probe oligonucleotide to hybridize to the reference oligonucleotide;
   d) detecting the detectable label; and
   e) chemically cleaving the cleavable linker to remove the detectable label and to allow the probe oligonucleotide to have a 5' phosphate group, wherein the probe oligonucleotide contains the same number of nucleotides after chemically cleaving the cleavable linker as it contained prior to cleavage, wherein the cleavable linker is a phosphoramidite linker.

41. The method of claim 40, wherein the cleavable linker is a phosphoramidite 1 linker.

42. The method of claim 40, wherein the cleavable linker is

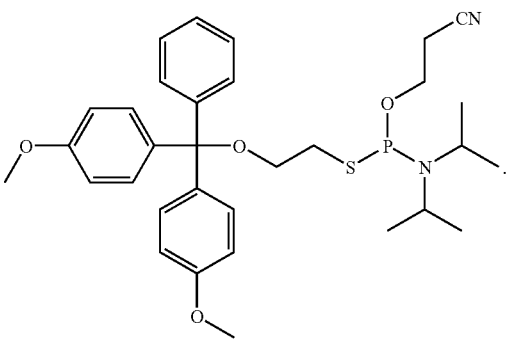 [SMILES: COc1ccc(C(OCCSP(OCCC#N)N(C(C)C)C(C)C)(c2ccccc2)c2ccc(OC)cc2)cc1 ; "."]

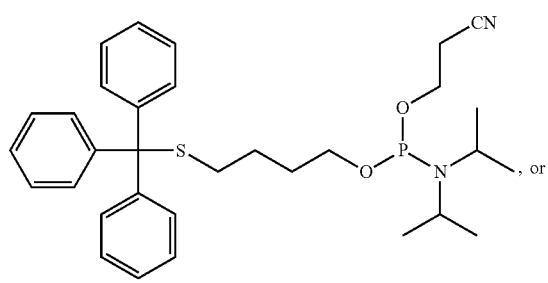 [SMILES: CC(C)N(C(C)C)P(OCCC#N)OCCCCSC(c1ccccc1)(c1ccccc1)c1ccccc1 ; ","]

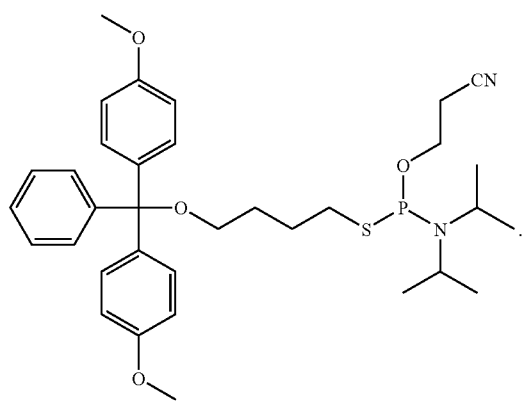 [SMILES: COc1ccc(C(OCCCCSP(OCCC#N)N(C(C)C)C(C)C)(c2ccccc2)c2ccc(OC)cc2)cc1 ; "."]

43. The method of claim 37, wherein the chemically cleaving step includes contacting the cleavable linker with one or more of AgNO$_3$ and I$_2$.

44. The method of claim 37, wherein the detectable label is a fluorophore.

45. The method of claim 37, wherein the probe oligonucleotide is a hexamer.

46. A method of determining a nucleotide sequence of a reference oligonucleotide comprising the steps of:
   a) providing a reference oligonucleotide;
   b) providing a probe oligonucleotide having a detectable label bound to its 5' phosphate group via a cleavable linker;
   c) allowing the probe oligonucleotide to hybridize to the reference oligonucleotide;
   d) detecting the detectable label; and
   e) chemically cleaving the cleavable linker to remove the detectable label and to allow the probe oligonucleotide to have a 3' phosphate group, wherein the probe oligonucleotide contains the same number of nucleotides after chemically cleaving the cleavable linker as it contained prior to cleavage.

47. The method of claim 46, wherein the cleavable linker includes an aliphatic backbone.

48. The method of claim 47, wherein the aliphatic backbone is between 2 and 24 carbons in length.

49. The method of claim 47, wherein the aliphatic backbone comprises at least one amide group, ether group, ketone group or ester group.

50. The method of claim 46, wherein the cleavable linker is a phosphoramidite linker.

51. The method of claim 46, wherein the cleavable linker is a phosphoramidite 1 linker.

52. The method of claim 46, wherein the cleavable linker is

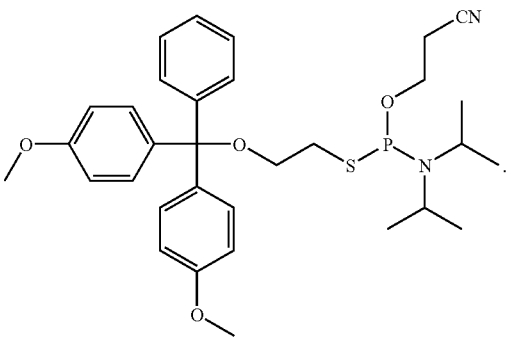 [SMILES: COc1ccc(C(OCCSP(OCCC#N)N(C(C)C)C(C)C)(c2ccccc2)c2ccc(OC)cc2)cc1 ; "."]

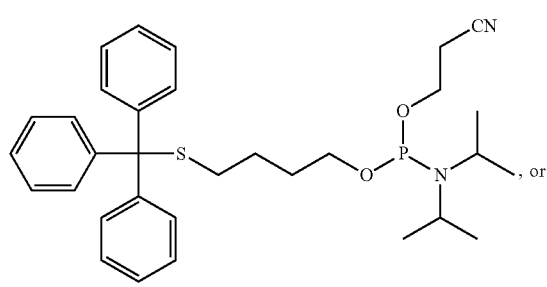 [SMILES: CC(C)N(C(C)C)P(OCCC#N)OCCCCSC(c1ccccc1)(c1ccccc1)c1ccccc1 ; ","]

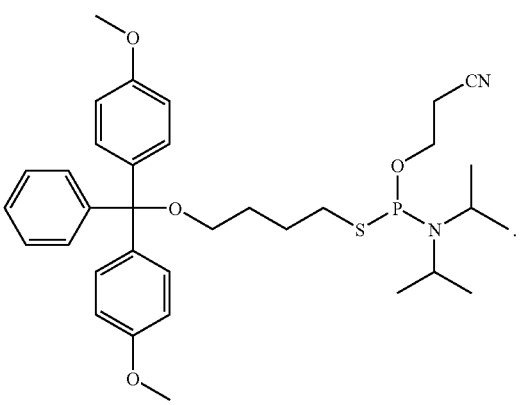 [SMILES: COc1ccc(C(OCCCCSP(OCCC#N)N(C(C)C)C(C)C)(c2ccccc2)c2ccc(OC)cc2)cc1 ; "."]

53. The method of claim 46, wherein the chemically cleaving step includes contacting the cleavable linker with one or more of AgNO$_3$ and I$_2$.

54. The method of claim 46, wherein the detectable label is a fluorophore.

55. The method of claim 46, wherein the probe oligonucleotide is a hexamer.

56. The method of claim 1 wherein the phosphoramidite 1 linker includes a dimethoxytrityl protected oxygen and a sulfur phosphoramidite.

57. The method of claim 10 wherein the phosphoramidite 1 linker includes a dimethoxytrityl protected oxygen and a sulfur phosphoramidite.

58. A method of determining a nucleotide sequence of a reference oligonucleotide comprising the steps of:
   a) providing a reference oligonucleotide;
   b) providing a probe oligonucleotide having a detectable label bound to its 5' phosphate group via a cleavable linker;

c) allowing the probe oligonucleotide to hybridize to the reference oligonucleotide;
d) detecting the detectable label; and
e) chemically cleaving the cleavable linker to remove the detectable label and to allow the probe oligonucleotide to have a 5' phosphate group, wherein the chemically cleaving step includes contacting the cleavable linker with one or more of $AgNO_3$ and $I_2$ and wherein the cleavable linker includes a dimethoxytrityl protected oxygen and a sulfur phosphoramidite.

59. A method of determining a nucleotide sequence of a reference oligonucleotide comprising the steps of:
a) providing a reference oligonucleotide;
b) providing a probe oligonucleotide having a detectable label bound to its 5' phosphate group via a cleavable linker;
c) allowing the probe oligonucleotide to hybridize to the reference oligonucleotide;
d) detecting the detectable label; and
e) chemically cleaving the cleavable linker to remove the detectable label and to allow the probe oligonucleotide to have a 3' phosphate group, wherein the chemically cleaving step includes contacting the cleavable linker with one or more of $AgNO_3$ and $I_2$ and wherein the cleavable linker includes a dimethoxytrityl protected oxygen and a sulfur phosphoramidite.

60. The method of claim 37 wherein the cleavable linker includes a dimethoxytrityl protected oxygen and a sulfur phosphoramidite.

61. The method of claim 46 wherein the cleavable linker includes a dimethoxytrityl protected oxygen and a sulfur phosphoramidite.

62. A method of determining a nucleotide sequence of a reference oligonucleotide comprising the steps of:
a) providing a reference oligonucleotide;
b) providing a probe oligonucleotide having a detectable label bound to its 5' phosphate group via a cleavable linker including an aliphatic backbone;
c) allowing the probe oligonucleotide to hybridize to the reference oligonucleotide;
d) detecting the detectable label; and
e) chemically cleaving the cleavable linker to remove the detectable label and to allow the probe oligonucleotide to have a 5' phosphate group.

63. The method of claim 62, wherein the aliphatic backbone is between 2 and 24 carbons in length.

64. The method of claim 62, wherein the aliphatic backbone comprises at least one amide group, ether group, ketone group or ester group.

* * * * *